US00PP24565P3

(12) United States Plant Patent
Egger

(10) Patent No.: US PP24,565 P3
(45) Date of Patent: Jun. 17, 2014

(54) ***HEUCHERA* PLANT NAMED 'SUGAR BERRY'**

(50) Latin Name: ***Heuchera* hybrid**
Varietal Denomination: Sugar Berry

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 144 days.

(21) Appl. No.: 13/507,974

(22) Filed: Aug. 10, 2012

(65) Prior Publication Data

US 2014/0047608 P1 Feb. 13, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by small silver leaves with prominent dark veins, spring and new leaves with a purple tint, light pink buds to white flowers on dark flower stalks, repeat blooming on short, dark flower stalks, a small, multi-crowned, low mounding habit, and excellent vigor.

1 Drawing Sheet

Botanical denomination: *Heuchera* hybrid.
Variety designation: 'Sugar Berry'.

BACKGROUND OF THE INVENTION

The present invention relates to a new and distinct cultivar of *Heuchera* and given the cultivar name of 'Sugar Berry'. *Heuchera* is in the family Saxifragaceae. *Heuchera* 'Sugar Berry' originated from a controlled cross between *Heuchera* K326-2, a proprietary non-commercial hybrid, as the seed parent, and *Heuchera* K326-4, a proprietary non-commercial hybrid, as, as the pollen parent.

Compared to the seed parent, *Heuchera* K326-2, the new cultivar has smaller leaves and with new leaves that have a purple tint rather than silver with dark veins.

Compared to the pollen parent, *Heuchera* K326-4, the new cultivar has an excellent crown count rather than a low crown count and shorter flowering stems.

Compared to *Heuchera* 'Shanghai', U.S. Plant Pat. No. 21,859, the new cultivar forms a lower mound that does not get "stemmy" over time, has light pink rather than cream colored flowers, has main veins that are prominently dark rather than all the veins, and leaves that are rounder with shallower leaf lobes.

This new *Heuchera* is uniquely distinguished by:

1. small silver leaves with prominent dark veins,
2. spring and new leaves with a purple tint
3. light pink buds to white flowers on dark flower stalks,
4. repeat blooming on short, dark flower stalks,
5. small, multi-crowned, low mounding habit, and
6. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a nine-month-old plant of *Heuchera* 'Sugar Berry' growing in a one gallon pot in a cool greenhouse in early July in Canby, Oreg.

DETAILED PLANT DESCRIPTION

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 2007 edition.

Plant:

*Form.*—Basal rosette, herbaceous perennial.
*Hardiness.*—USDA Zone 4 to 9.
*Size.*—17 cm tall from top of the foliage to the soil and 37 cm wide.
*Habit.*—Mounding.
*Vigor.*—Excellent.

Leaf:

*Type.*—Simple.
*Arrangement.*—Rosette.
*Shape.*—Broadly ovate to orbicular.
*Lobing/division.*—5 to 7 shallow lobes.
*Venation.*—Palmate.
*Margins.*—Crenate, slightly wavy.
*Apex.*—Mucronulate.
*Base.*—Cordate.
*Blade size.*—Grows to 7 cm long and 6.5 cm wide.

*Texture.*—Supple.

*Surface texture.*—Glandular on top and bottom side.

*Petiole description.*—Grows to 14 cm long and 2 mm wide, glandular hairs, Greyed Purple 187A.

*Leaf color.*—Topside, new leaves in spring between Purple 79A and Purple N77C with veins Greyed Purple N186A, bottom side closest to Purple N77A; summer leaves closest to Black 202B tinted Purple 79A with veins Black 203D; winter leaves are closest to Black 202B with veins Black 203D, bottom side Greyed Purple N187A.

Inflorescence:

*Size.*—Grows to 3.5 cm wide and 9 cm long.

*Type.*—Thyrse.

*Number of flowers per thyrse.*—About 60.

*Number of thyrse.*—About 5 in the first spring flush, reblooming all summer to frost.

*Peduncle.*—Grows to 20 cm long, 3 mm wide at base, Purple N77A, glandular hairs.

*Pedicel.*—Variable in size, with glandular hairs, Purple N77A.

*Bloom period.*—May through October in Canby, Oreg.

Flower bud:

*Size.*—2 mm wide and 2 mm long.

*Description.*—Glandular puberulent, ovoid, down facing.

*Color.*—Red Purple 65B on the bottom ⅓ and 62D on the top ⅔.

Flower:

*Type.*—Perfect.

*Shape.*—Campanulate.

*Size.*—5 mm long and 3.5 mm wide.

*Corolla description.*—5 petals, 2 mm long and 0.5 mm wide, narrowly spatulate, margins entire, tip acute, glabrous top and glandular on bottom, White NN155C.

*Calyx description.*—Campanulate, 5 mm long and 3.5 mm wide, with 5 lobes divided ½ way to the base, each 2 mm wide and 3.5 mm long, glandular hairs outside and inside, tips obtuse, margin entire; color outside and inside NN155B with tints of Red Purple 62D on outside lobe tips and base.

*Stamen description.*—5 in number, filaments 1.5 mm long, White NN155C, anthers 0.2 mm, Orange 26A, pollen none.

*Pistil description.*—1, 2-beaked, 4 mm long and 2 mm wide, Red Purple 69C overall; ovary 1.5 mm long and 2 mm wide, style 2.5 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Number.*—About 40.

*Color.*—Greyed Brown 199C.

*Size.*—4 mm long and 3 mm wide.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

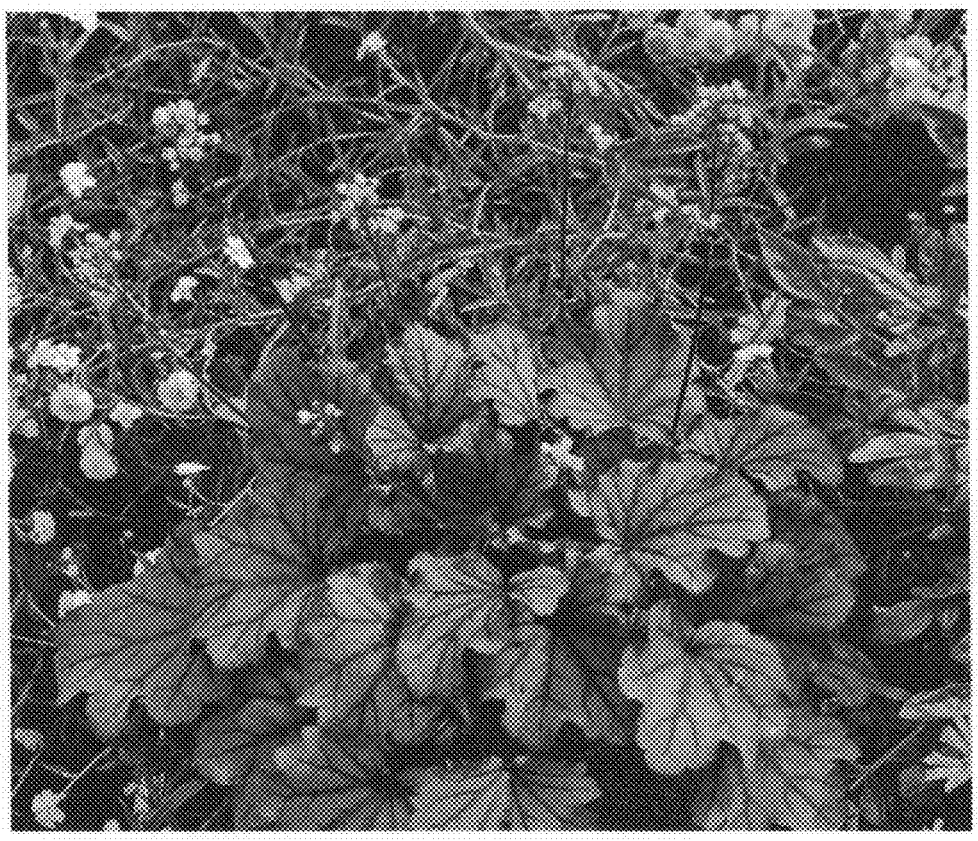

* * * * *